United States Patent [19]

Moheno

[11] Patent Number: 5,534,514
[45] Date of Patent: Jul. 9, 1996

[54] ANTI-NEOPLASTIC COMPOSITIONS AND METHODS FOR APPLICATION THEREOF

[75] Inventor: Phillip B. B. Moheno, La Jolla, Calif.

[73] Assignee: San Diego State University, San Diego, Calif.

[21] Appl. No.: 445,794

[22] Filed: May 22, 1995

Related U.S. Application Data

[63] Continuation of Ser. No. 967,283, Oct. 27, 1992, abandoned.

[51] Int. Cl.$^6$ .......................... A61K 31/495; A61K 31/50
[52] U.S. Cl. ............................................................. 514/249
[58] Field of Search .................................................. 514/249

[56] References Cited

U.S. PATENT DOCUMENTS

| | | |
|---|---|---|
| 2,437,853 | 3/1948 | Hitchings . |
| 2,440,221 | 4/1948 | Hitchings . |
| 4,156,725 | 5/1979 | Wood et al. . |
| 4,393,064 | 7/1983 | Degraw, Jr. et al. . |
| 4,753,939 | 6/1988 | Degraw, Jr. et al. . |
| 4,758,571 | 7/1988 | Curtius et al. . |
| 4,820,706 | 4/1989 | Khaled et al. . |

OTHER PUBLICATIONS

*The Press Courier*, Jan. 17, 1982, "Professor Experiments With Potential Cancer Cure".
*University News* of California State University, Spring 1988, "Teaching and research go hand in hand".

*Primary Examiner*—Jerome D. Goldberg
*Attorney, Agent, or Firm*—Fish & Richardson

[57] ABSTRACT

Anti-neoplastic compositions consisting of one or more pterins, or derivatives or analogs thereof, selected from the group consisting of xanthopterin, isoxanthopterin and/or neopterin, and/or a derivative or analog thereof, and a method for the application thereof to a living creature in an amount and composition which, in the preferred embodiment, consists of substantially about 32 micrograms per milliliter xanthopterin and substantially about 16 micrograms per milliliter isoxanthopterin suspension diluted in an inert carrier and administered subcutaneously into the vicinity of the neoplasm with a frequency sufficient to inhibit the growth of the neoplasm.

4 Claims, 3 Drawing Sheets

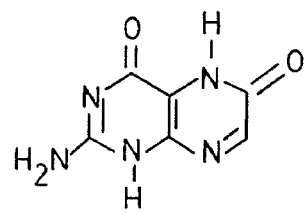
XANTHOPTERIN
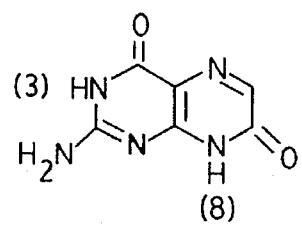  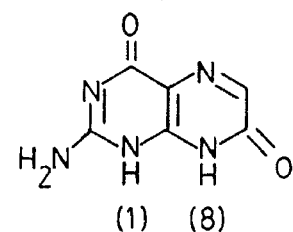
ISOXANTHOPTERIN
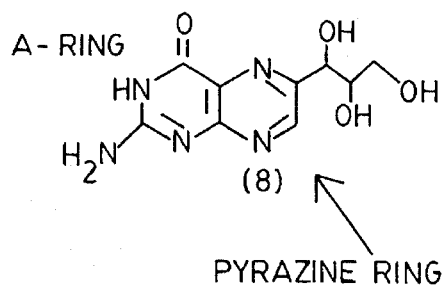 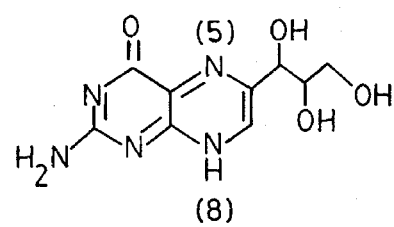
NEOPTERIN
FIG. 2

ANTI-NEOPLASTIC COMPOSITIONS AND METHODS FOR APPLICATION THEREOF

This is a continuation of application Ser. No. 07/967,283, filed Oct. 27, 1992, now abandoned.

BACKGROUND OF THE INVENTION

1. Field of the Invention

The present invention relates to anti-neoplastic compositions and methods for application thereof and, more particularly, to such compositions and methods which have been discovered to be of particular value in the treatment of tumors, particularly of the cancerous type.

2. Description of the Prior Art

Research has heretofore recognized the therapeutic value of certain pterins in the treatment of certain forms of neoplastic disease. For example, the DeGraw, Jr. et at. U.S. Pat. No. 4,393,064 discloses a process in composition for the treatment of leukemia using 10-deazaminopterin. Similarly, the DeGraw, Jr. et at. U.S. Pat. No. 4,753,939 discloses another process and composition for the treatment of leukemia employing 10-ethyl-10 deazaminopterin. Other pterin derivatives have been discovered to have properties beneficial in the treatment of certain diseases. For example, the Curtius et al. U.S. Pat. No. 4,758,571 discloses that L-erythro-5,6,7,8-tetrahydrobiopterin, L-sepiapterin, 1',2'-diacetyl-5,6,7,8-tetrahydrobiopterin and 6-methyl-5,6,7,8-tetrahydropterin can beneficially be used in the treatment of patients having Parkinson's disease and of patients exhibiting depression. Still further, the Khaled et at. U.S. Pat. No. 4,820,706 discloses the use of pteridine derivatives in treating leukemia.

While the salutary effects of such compositions have been known, there has not heretofore previously been a composition of pterins which has exhibited the capability for reducing the volume of neoplastic masses in living creatures regardless of the type, volume or age of the neoplastic mass so as to offer the possibility of remedial treatment in substantially all physiological forms in which such neoplasms evidence themselves.

Therefore, it has long been known that it would be desirable to have anti-neoplastic compositions and methods for application thereof which are capable of therapeutically treating virtually all neoplasms regardless of the form, volume, location and state of development having application to humans and virtually all mammalian creatures and substantially without the detrimental effects characterized by conventional chemotherapy.

SUMMARY OF THE INVENTION

Therefore, it is an object of the present invention to provide anti-neoplastic compositions and methods for application thereof.

Another object is to provide such compositions and methods which can be therapeutically employed in the treatment of virtually all neoplasms operable to reduce both the volume of the masses and morbidity associated therewith.

Another object is to provide such compositions and methods which can remedially be employed in the treatment of such neoplasms in virtually all mammalian creatures including humans.

Another object is to provide such compositions and methods which can be employed with beneficial results irrespective of the type of neoplasm, the volume of the neoplasm, or the age thereof.

Another object is to provide such compositions and methods which can conveniently and dependably be employed using a substantially noninvasive means for application and one which is fully compatible with conventional medical techniques.

Another object is to provide such compositions and methods which can be administered without the detrimental side effects associated with conventional compositions and methods and which require a minimal amount of equipment and medical expertise in the application thereof.

Another object is to provide such compositions and methods which have such wide beneficial application as to constitute a virtually universal treatment for neoplasms.

These and other objects and advantages are achieved, in the preferred embodiment of the compositions and methods of the present invention, in an anti-neoplastic composition consisting essentially of an effective amount of a mixture of a pterin diluted in an inert carrier and applied in an amount and frequency sufficient to inhibit the growth of the neoplasm.

BRIEF DESCRIPTION OF THE DRAWINGS

FIG. 2 is a diagrammatic view depicting the chemical structures of xanthopterin, isoxanthopterin and neopterin employed in the compositions and methods of the present invention.

DESCRIPTION OF THE PREFERRED EMBODIMENTS

First Embodiment

Figure 1:
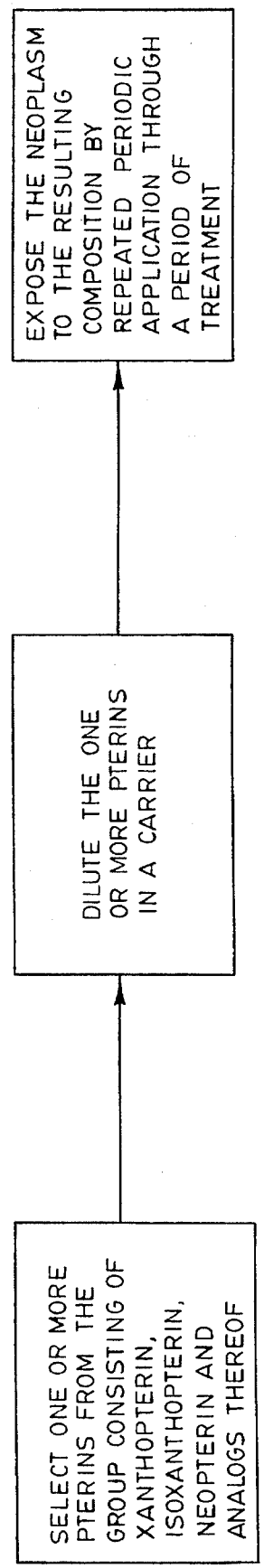
FIG. 1 is a diagrammatic view depicting the steps in the formulation of the compositions of the present invention and the method for the use thereof.
Figure 3:
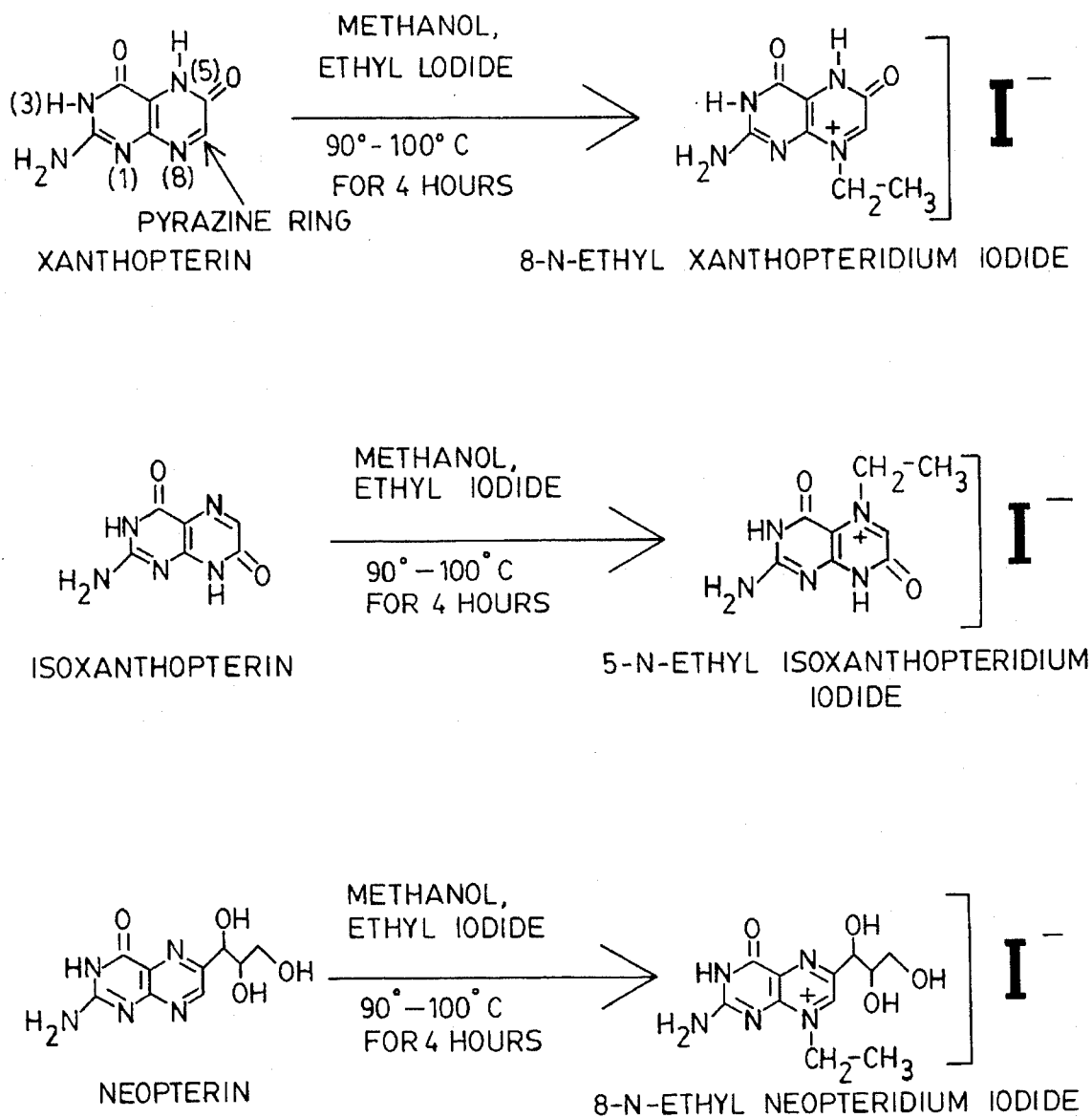
FIG. 3 is a diagrammatic view depicting the formulation of representative analogs of xanthopterin, isoxanthopterin and neopterin employed in the compositions and methods of the present invention, the analogs respectively being 8-N-ethyl xanthopteridium iodide, 5-N-ethyl isoxanthopteridium iodide and 8-N-ethyl neopteridium iodide.

Referring more particularly to the drawings, the anti-neoplastic compositions and methods for application thereof of the present invention are shown diagrammatically in FIG. 1. The compositions are a formulation of a pterin selected from the group consisting of xanthopterin, isoxanthopterin, neopterin and derivatives and analogs thereof. It has been discovered that these three pterins and derivatives and analogs thereof, work together synergistically to demonstrate significant anti-neoplastic activity. One such analog is 8-ethyl-xanthopteridium iodide. While, as will subsequently be disclosed in greater detail, certain formulations of the compositions of the present invention have been found to evidence stronger responses against larger or smaller neoplasms, the beneficial effects over all are consistent and such variables are believed to constitute species of the invention having particular utility relative to neoplasms of specific characteristics, but otherwise evidencing remedial effects when applied to all neoplasms.

EXAMPLE I

In Example I, a mixture of substantially about 32 micrograms per milliliter xanthopterin and substantially about 16 micrograms per milliliter isoxanthopterin suspension were diluted in an inert carrier, preferably about 0.2 milliliters Mammalian Ringer's Solution. For convenience, this mixture will hereinafter be referred to as the "XIpterin mixture".

Using the XIpterin mixture, a number of a strain of black mice identified as "C58/J" acquired from The Jackson Laboratory, Animal Resources of Bar Harbor, Me. were employed in laboratory tests. The C58/J strain of black mice has approximately a 90 per cent incidence of lymphocytic leukemia characterized by tumor masses in the thymus, spleen and lymph nodes. The mean latent period of mortality is 318 days, or 10.6 months, with tumors appearing as early as 5 months of age. The test mice were acquired at approximately 10 weeks of age from Jackson Laboratories.

The experimental data hereinafter set forth result from experiments on 42 of the C58/J black mice running in age from 22 to 31 weeks. Each mouse was randomly assigned to either the experimental or control group. Each mouse in the experimental group, which numbered 20 mice, received injections of the Xipterin mixture, consisting of 32 micrograms per milliliter xanthopterin and 16 micrograms per milliliter isoxanthopterin suspension in 0.2 milliliters Mammalian Ringer's Solution. The injections were administered subcutaneously. The mice in the control group, which numbered 22 mice, received subcutaneous injections of 0.2 milliliters Mammalian Ringer's Solution not containing a pterin or any other substance. The injection volumes were carefully controlled so that both groups received the same amounts. The injection schedule was as follows:

| C58/J Injection Schedule | | | | | |
|---|---|---|---|---|---|
| Date | Injection Vol. | Date | Injection Vol. | Date | Injection Vol. |
| 12/23/88 | 0.2 mL | 05/04/89 | 0.2 mL | 09/13/89 | 0.1 Ml |
| 01/03/89 | 0.2 Ml | 05/06/89 | 0.2 mL | 09/21/89 | 0.15 Ml |
| 01/06/89 | 0.2 Ml | 05/09/89 | 0.2 mL | 10/03/89 | 0.15 Ml |
| 01/10/89 | 0.2 Ml | 05/11/89 | 0.2 mL | 10/12/89 | 0.2 mL |
| 01/13/89 | 0.2 mL | 05/13/89 | 0.2 mL | 10/17/89 | 0.2 mL |
| 01/17/89 | 0.2 mL | 05/15/89 | 0.2 mL | 10/19/89 | 0.2 mL |
| 01/20/89 | 0.4 mL | 05/16/89 | 0.2 mL | 10/24/89 | 0.2 mL |
| 01/24/89 | 0.2 mL | 05/18/89 | 0.2 mL | 10/27/89 | 0.2 mL |
| 01/27/89 | 0.2 mL | 05/20/89 | 0.2 mL | 11/01/89 | 0.2 mL |
| 01/31/89 | 0.2 mL | 05/22/89 | 0.2 mL | 11/04/89 | 0.2 mL |
| 02/03/89 | 0.2 mL | 05/23/89 | 0.2 mL | 11/08/89 | 0.2 mL |
| 02/07/89 | 0.2 mL | 05/25/89 | 0.2 mL | 11/11/89 | 0.2 mL |
| 02/10/89 | 0.2 mL | 05/27/89 | 0.2 mL | 11/15/89 | 0.2 mL |
| 02/14/89 | 0.2 mL | 05/29/89 | 0.2 mL | 11/18/89 | 0.2 mL |
| 02/17/89 | 0.2 mL | 05/30/89 | 0.2 mL | 11/22/89 | 0.2 mL |
| 02/21/89 | 0.2 mL | 06/01/89 | 0.2 mL | 12/02/89 | 0.2 mL |
| 04/11/89 | 0.2 mL | 06/27/89 | 0.2 mL | 12/06/89 | 0.2 mL |
| 04/12/89 | 0.2 mL | 06/30/89 | 0.2 mL | 12/09/89 | 0.2 mL |
| 04/13/89 | 0.2 mL | 07/04/89 | 0.2 mL | 12/13/89 | 0.2 mL |
| 04/14/89 | 0.2 mL | 08/30/89 | 0.1 mL | 12/16/89 | 0.2 mL |
| 04/19/89 | 0.2 mL | 09/02/89 | 0.1 mL | 12/20/89 | 0.2 mL |
| 05/02/89 | 0.2 mL | 09/06/89 | 0.1 mL | | |

The C58/J mice generally do not produce palpable tumors. Accordingly, during the course of the injection schedule, the responses of the mice in both the experimental and control groups was monitored by noting weight changes and evaluating the over all vigor of each mouse. In this manner, the researchers attempted to discern the therapeutic window of efficacy for the regimen of application of the XIpterin mixture. However, these indices proved to be unreliable for discerning the anti-cancer therapeutic effectiveness of the regimen on a day-by-day basis.

The age of mortality of each mouse was the critical dependent variable in this experiment. The data relative to age of mortality was analyzed using the one-tailed t-test on the mean life expectancies of the two groups of mice. This was done under the null hypothesis, $H_o: M_e \leq M_c$, and using an $\infty$ (alpha)=0.05 to reject the null hypothesis, where $M_e$ is the mean age of mortality of the experimental group and $M_c$ is the mean age of mortality of the control group.

Other general observations were made and daily records kept. These observations included the position and size of any noticeable tumors for each mouse and necropsy results on each expired C58/J mouse. The necropsies included looking at the condition of the internal organs as well as for the presence of any internal tumors. The resulting data from Example I using all the mouse data are shown in Table 1 as follows:

TABLE 1

C58/J Female Mice
Unpaired t-Test $X_1$: Mouse Assignment $Y_1$: Life Expectancy

| DF: | Unpaired t Value: | Prob. (1-tail): |
|---|---|---|
| 40 | −.727 | .2358 |

| Group: | Count: | Mean: | Std. Dev.: | Std. Error: |
|---|---|---|---|---|
| Control | 22 | 290.227 | 77.003 | 16.417 |
| Experimental | 20 | 308.75 | 88.145 | 19.71 |

As shown in Table 1, the mean age of mortality of the experimental group of C58/J mice was increased by 6.4%. This increase, however, was not believed significant (p=0.2358). Tables 2, 3, 4, 5 and 6 show the same data successively trimmed for robustness; that is, in Table 2 the high and low values are thrown out from both the experimental and control groups; in Table 3 the next high and low values for each group were excluded from the analysis; and in Table 4 the next high and low values for each group were eliminated. The analyses shown in Tables 5 and 6 were similarly trimmed. As can be seen, the significance of the test improves with the robustness of the analysis (p=0.1213 in Table 5, with a 7.7% increase in life expectancy).

TABLE 2

C58/J Female Mice
Unpaired t-Test $X_1$: Mouse Assignment $Y_1$: Life Expectancy - Robust

| DF: | Unpaired t Value: | Prob. (1-tail): |
|---|---|---|
| 36 | −.84 | .2032 |

| Group: | Count: | Mean: | Std. Dev.: | Std. Error: |
|---|---|---|---|---|
| Control | 20 | 286.25 | 63.755 | 14.256 |
| Experimental | 18 | 304.778 | 72.221 | 17.023 |

TABLE 3

C58/J Female Mice
Unpaired t-Test $X_1$: Mouse Assignment $Y_1$: Life Expectancy - Robust 2

| DF: | Unpaired t Value: | Prob. (1-tail): |
|---|---|---|
| 32 | −.894 | .1889 |

| Group: | Count: | Mean: | Std. Dev.: | Std. Error: |
|---|---|---|---|---|

TABLE 3-continued

C58/J Female Mice
Unpaired t-Test $X_1$: Mouse Assignment $Y_1$: Life Expectancy - Robust 2

| Control | 18 | 285.111 | 58.79 | 13.857 |
|---|---|---|---|---|
| Experimental | 16 | 303.062 | 57.984 | 14.496 |

TABLE 4

C58/J Female Mice
Unpaired t-Test $X_1$: Mouse Assignment $Y_1$: Life Expectancy - Robust 3

| DF: | Unpaired t Value: | Prob. (1-tail): |
|---|---|---|
| 28 | −1.038 | .1539 |

| Group: | Count: | Mean: | Std. Dev.: | Std. Error: |
|---|---|---|---|---|
| Control | 16 | 284.562 | 53.79 | 13.447 |
| Experimental | 14 | 304.429 | 50.468 | 13.488 |

TABLE 5

C58/J Female Mice
Unpaired t-Test $X_1$: Mouse Assignment $Y_1$: Life Expectancy - Robust 4

| DF: | Unpaired t Value: | Prob. (1-tail): |
|---|---|---|
| 24 | −1.198 | .1213 |

| Group: | Count: | Mean: | Std. Dev.: | Std. Error: |
|---|---|---|---|---|
| Control | 14 | 284 | 47.839 | 12.786 |
| Experimental | 12 | 305.917 | 44.844 | 12.945 |

TABLE 6

C58/J Female Mice
Unpaired t-Test $X_1$: Mouse Assignment $Y_1$: Life Expectancy - Robust 5

| DF: | Unpaired t Value: | Prob. (1-tail): |
|---|---|---|
| 20 | −1.149 | .132 |

| Group: | Count: | Mean: | Std. Dev.: | Std. Error: |
|---|---|---|---|---|
| Control | 12 | 284.833 | 44.472 | 12.838 |
| Experimental | 10 | 305.8 | 40.216 | 12.717 |

The raw data of Example I is shown in the following corresponding Tables 1A, 2A, 3A, 4A, 5A and 6A where Table 1A contains the complete data for Table 1; Table 2A contains the complete data for Table 2, and so on.

TABLE 1A

Complete Data

| Age of Expiration (Experimental) - in descending order | Age of Expiration (Control) - in descending order |
|---|---|
| 512 | 478 |
| 456 | 392 |
| 386 | 377 |
| 369 | 371 |
| 368 | 342 |
| 366 | 334 |
| 362 | 330 |
| 345 | 324 |

TABLE 1A-continued

Complete Data

| Age of Expiration (Experimental) - in descending order | Age of Expiration (Control) - in descending order |
|---|---|
| 312 | 320 |
| 308 | 313 |
| 289 | 305 |
| 280 | 294 |
| 276 | 272 |
| 269 | 267 |
| 251 | 222 |
| 245 | 221 |
| 222 | 216 |
| 201 | 216 |
| 181 | 206 |
| 177 | 202 |
|  | 201 |
|  | 182 |
| mean = 308.8 days | mean = 290.2 days |

Unpaired t-Value (df = 40) = −.727
p (one-tail) = .24

TABLE 2A

Robust-1 Data

| Age of Expiration (Experimental) - in descending order | Age of Expiration (Control) - in descending order |
|---|---|
| 456 | 392 |
| 386 | 377 |
| 369 | 371 |
| 368 | 342 |
| 366 | 334 |
| 362 | 330 |
| 345 | 324 |
| 312 | 320 |
| 308 | 313 |
| 289 | 305 |
| 280 | 294 |
| 276 | 272 |
| 269 | 267 |
| 251 | 222 |
| 245 | 221 |
| 222 | 216 |
| 201 | 216 |
| 181 | 206 |
|  | 202 |
|  | 201 | mean = 304.8 days        mean = 286.2 days
Unpaired t-Value (df = 36) = −.84
p (one-tail) = .20

TABLE 3A

Robust-2 Data

| Age of Expiration (Experimental) -in descending order | Age of Expiration (Control) - in descending order |
|---|---|
| 386 | 377 |
| 369 | 371 |
| 368 | 342 |
| 366 | 334 |
| 362 | 330 |
| 345 | 324 |
| 312 | 320 |
| 308 | 313 |
| 289 | 305 |
| 280 | 294 |
| 276 | 272 |

TABLE 3A-continued

Robust-2 Data

| Age of Expiration (Experimental) -in descending order | Age of Expiration (Control) - in descending order |
| --- | --- |
| 269 | 267 |
| 251 | 222 |
| 245 | 221 |
| 222 | 216 |
| 201 | 216 |
| . | 206 |
| . | 202 |
| . | . |
| mean = 303.1 days | mean = 285.1 days |
| Unpaired t-Value (df = 32) = −.894 | |
| p (one-tail) = .19 | |

TABLE 4A

Robust-3 Data

| Age of Expiration (Experimental) -in descending order | Age of Expiration (Control) - in descending order |
| --- | --- |
| . | . |
| . | . |
| 369 | 371 |
| 368 | 342 |
| 366 | 334 |
| 362 | 330 |
| 345 | 324 |
| 312 | 320 |
| 308 | 313 |
| 289 | 305 |
| 280 | 294 |
| 276 | 272 |
| 269 | 267 |
| 251 | 222 |
| 245 | 221 |
| 222 | 216 |
| . | 216 |
| . | 206 |
| . | . |
| mean = 304.4 days | mean = 284.6 days |
| Unpaired t-Value (df = 28) = −1.038 | |
| p (one-tail) = .15 | |

TABLE 5A

Robust-4 Data

| Age of Expiration (Experimental) -in descending order | Age of Expiration (Control) - in descending order |
| --- | --- |
| . | . |
| . | . |
| . | . |
| 368 | 342 |
| 366 | 334 |
| 362 | 330 |
| 345 | 324 |
| 312 | 320 |
| 308 | 313 |
| 289 | 305 |
| 280 | 294 |
| 276 | 272 |
| 269 | 267 |
| 251 | 222 |
| 245 | 221 |
| . | 216 |
| . | 216 |

TABLE 5A-continued

Robust-4 Data

| Age of Expiration (Experimental) -in descending order | Age of Expiration (Control) - in descending order |
| --- | --- |
| . | . |
| . | . |
| mean = 305.9 days | mean = 284.0 days |
| Unpaired t-Value (df = 24) = −1.198 | |
| p (one-tail) = .12 | |

TABLE 6A

Robust-5 Data

| Age of Expiration (Experimental) -in descending order | Age of Expiration (Control) - in descending order |
| --- | --- |
| . | . |
| . | . |
| . | . |
| . | . |
| 366 | 334 |
| 362 | 330 |
| 345 | 324 |
| 312 | 320 |
| 308 | 313 |
| 289 | 305 |
| 280 | 294 |
| 276 | 272 |
| 269 | 267 |
| 251 | 222 |
| . | 221 |
| . | 216 |
| . | . |
| . | . |
| . | . |
| mean = 305.8 days | mean = 284.8 days |
| Unpaired t-Value (df = 20) = −1.149 | |
| p (one-tail) = .13 | |

EXAMPLE II

The same XIpterin mixture of Example I was employed in Example II on a strain of mice identified as "C3H/Ou" purchased from The Jackson Laboratory. The C3H/Ou mice produce externally palpable mammary tumors. One hundred percent (100%) of this strain of mice are reported to produce mammary tumors by 44 weeks of age. As noted, the mammary tumors produced by this mouse strain are easily palpable and measurable using a caliper.

In this example, retired female C3H/Ou breeders were purchased along with information relating to the date of birth of each mouse and to the number of litters each had had. The mice were first housed for evaluation and then introduced into the experiment in pairs as each produced a palpable tumor. Initially, each C3H/Ou mouse was introduced into the experiment when at least one of its tumors reached 10 millimeters in diameter. After the few mice were so introduced into the experiment, the criteria were modified to the extent that each mouse was introduced as soon as it presented any palpable tumor.

The experimental mice were labeled AE, BE, CE, DE, FE, GE and HE wherein, of course, the "E" identifies a mouse of the experimental group. Each of the mice of the experimental group was started on the XIpterin mixture by subcutaneous injection in accordance with the schedule previously described in reference to Example I. To reiterate, the XIpterin mixture consists of 32 micrograms per milliliter xanthopterin and 16 micrograms per milliliter isoxanthopterin suspension in 0.2 milliliters Mammalian Ringer's Solution. The control mice were labeled AC, BC, CC, DC, EC, FC, GC and HC wherein, of course, the "C" signifies the control group. The mice of the control group were given identical subcutaneous injections in accordance with the same regimen as that of the experimental group. However, the injections used Mammalian Ringer's Solution without the XIpterin mixture or any other substance.

Daily animal weight and tumor diameter measurements were recorded for each mouse. The longest diameters for non-spherical tumors were initially recorded, but after a few mice, the average tumor diameters for the few non-spherical tumors which arose were recorded. This approach was adopted because the data was used to calculate tumor volumes under the assumption that the tumors were spherical.

Tables 7A through 7H are summaries of the 8 C3H/Ou mice of the experimental and control groups of the test of Example II analyzed in this manner.

The data which shows the manner in which the test results were evaluated. Briefly, total tumor volumes were calculated daily and the daily differences between the paired experimental and control mice were calculated. Then a simple linear regression was calculated and the slope of the regression was used as the dependent measure of anti-tumor efficacy.

TABLE 7A

Mouse Pair - A

| Day | Total Tumor Volume (mm³) (Experimental) | Total Tumor Volume (mm³) (Control) | Total Tumor Volume (mm³) (Experimental minus Control) |
| --- | --- | --- | --- |
| 1 | 974.4 | 523.6 | 450.8 |
| 2 | 1317.2 | 606.2 | 711.0 |
| 3 | 755.5 | 539.5 | 216.0 |
| 4 | 1022.7 | 572.2 | 450.5 |
| 5 | 1231.9 | 659.6 | 572.3 |
| 6 | 1531.2 | 623.6 | 907.5 |
| 7 | 1949.9 | 882.4 | 1067.5 |
| 8 | 1987.9 | 882.4 | 1105.5 |
| 9 | 1732.1 | 1663.3 | 68.8 |
| 10 | 1767.2 | 1697.5 | 69.8 |
| 11 | 2309.7 | 1177.2 | 1132.5 |
| 12 | 2226.2 | 1259.9 | 966.3 |
| 13 | 2026.4 | 1204.3 | 822.1 |
| 14 | 1767.2 | 1732.1 | 35.1 |
| 15 | 2482.8 | 2395.2 | 87.6 |
| 16 | 3209.0 | 2309.7 | 899.3 |

TABLE 8B

Mouse Pair - B

| Day | Total Tumor Volume (mm³) (Experimental) | Total Tumor Volume (mm³) (Control) | Total Tumor Volume (mm³) (Experimental minus Control) |
| --- | --- | --- | --- |
| 1 | 1225.9 | 523.6 | 702.3 |
| 2 | 1637.8 | 523.6 | 1114.2 |
| 3 | 1269.6 | 641.5 | 628.2 |
| 4 | 1276.7 | 735.7 | 541.0 |
| 5 | 1444.0 | 1259.9 | 184.1 |
| 6 | 1276.7 | 1177.2 | 99.5 |
| 7 | 1408.5 | 1259.9 | 148.7 |
| 8 | 1487.1 | 1346.4 | 140.7 |
| 9 | 885.5 | 1406.3 | −520.7 |
| 10 | 1381.7 | 1531.2 | −149.4 |
| 11 | 1601.4 | 1875.4 | −274.0 |
| 12 | 1421.1 | 1976.8 | −555.6 |
| 13 | 1417.6 | 2202.6 | −785.0 |
| 14 | 1279.9 | 2976.0 | −1696.1 |
| 15 | 1444.8 | 2625.1 | −1180.3 |
| 16 | 1187.4 | 3308.0 | −2120.6 |
| 17 | 1606.6 | 2685.6 | −1079.0 |
| 18 | 1533.2 | 2687.6 | −1154.4 |
| 19 | 1903.3 | 4402.9 | −2499.7 |
| 20 | 3839.7 | 3389.6 | 450.2 |
| 21 | 3076.4 | 3855.8 | −779.4 |
| 22 | 4327.1 | 4024.5 | 302.6 |
| 23 | 5835.0 | 3612.1 | 2222.9 |
| 24 | 5192.6 | 4729.8 | 462.8 |
| 25 | 5224.7 | 4366.3 | 858.4 |
| 26 | 5216.6 | 5769.4 | −552.8 |
| 27 | 5856.4 | 5959.6 | −103.2 |
| 28 | 5449.3 | 6601.7 | −1152.4 |
| 29 | 5918.0 | 7434.0 | −1516.0 |
| 30 | 6379.3 | 7646.4 | −1267.1 |
| 31 | 7278.7 | 8637.6 | −1358.9 |
| 32 | 6956.7 | 9916.0 | −2959.3 |
| 33 | 8979.2 | 9440.4 | −461.2 |
| 34 | 10076.0 | 9904.1 | 171.9 |
| 35 | 10839.9 | 11089.2 | −249.3 |
| 36 | 11030.1 | 12905.0 | −1874.9 |
| 37 | 10823.8 | 13334.1 | −2510.3 |
| 38 | 12217.3 | 15188.9 | −2971.6 |
| 39 | 11087.4 | 15628.2 | −4540.8 |
| 40 | 10173.8 | 13511.3 | −3337.5 |
| 41 | 12934.1 | 12422.4 | 511.7 |
| 42 | 12968.1 | 14423.9 | −1455.8 |
| 43 | 13354.9 | 12955.3 | 399.6 |
| 44 | 13279.0 | 14182.3 | −903.3 |

TABLE 7C

Mouse Pair - C

| Day | Total Tumor Volume (mm³) (Experimental) | Total Tumor Volume (mm³) (Control) | Total Tumor Volume (mm³) (Experimental minus Control) |
| --- | --- | --- | --- |
| 1 | 555.7 | 1764.0 | −1208.3 |
| 2 | 882.4 | 1982.9 | −1100.5 |
| 3 | 1124.1 | 1855.4 | −731.3 |
| 4 | 641.5 | 1442.8 | −801.3 |
| 5 | 623.6 | 2022.8 | −1399.2 |
| 6 | 539.5 | 2279.5 | −1740.0 |
| 7 | 678.1 | 3041.7 | −2363.6 |
| 8 | 606.2 | 2853.9 | −2247.7 |
| 9 | 775.8 | 3069.3 | −2293.5 |
| 10 | 882.4 | 3416.1 | −2533.7 |
| 11 | 1098.1 | 3254.8 | −2156.7 |
| 12 | 1317.2 | 3404.3 | −2087.2 |
| 13 | 1288.3 | 3733.0 | −2444.6 |
| 14 | 1531.2 | 3689.0 | −2157.8 |
| 15 | 2065.3 | 3778.2 | −1712.9 |
| 16 | 2104.8 | 4303.3 | −2198.5 |
| 17 | 1767.2 | 4572.1 | −2804.4 |
| 18 | 2661.1 | 4324 | −1662.2 |
| 19 | 4134.6 | 4613.4 | −477.9 |
| 20 | 3615.3 | 7520.3 | −3904.2 |
| 21 | 3296.3 | 8123.1 | −4826 |

TABLE 7C-continued

Mouse Pair - C

| Day | Total Tumor Volume ($mm^3$) (Experimental) | Total Tumor Volume ($mm^3$) (Control) | Total Tumor Volume ($mm^3$) (Experimental minus Control) |
|---|---|---|---|
| 22 | 3756.8 | 9732.9 | −5975.2 |
| 23 | 4696.0 | 8174.5 | −3477.4 |
| 24 | 3696.6 | 9793.3 | −6095.8 |
| 25 | 4263.1 | 9206.7 | −4942.6 |
| 26 | 4575.3 | 10198.9 | −5622.5 |
| 27 | 4684.0 | 11856.1 | −7170.9 |
| 28 | 4852.9 | 7316.9 | −2462.9 |
| 29 | 4997.8 | 9062.6 | −4063.6 |
| 30 | 6433.3 | 7678 | −1243.1 |
| 31 | 6700.0 | 8439.8 | −1738.2 |
| 32 | 6823.1 | 12113.3 | −5288.6 |
| 33 | 8708.7 | 13299.1 | −4588.4 |
| 34 | 8514.4 | 11394.7 | −2878.2 |
| 35 | 8275.5 | 11647 | −3369.6 |
| 36 | 8315.5 | 11903.3 | −3585.8 |
| 37 | 8825.7 | 12448.3 | −3620.5 |
| 38 | 7529.3 | 18266 | −10734.9 |
| 39 | 8708.9 | 24516.5 | −15805.5 |
| 40 | 10153.4 | 19153.3 | −8997.5 |
| 41 | 10266.1 | 16887.9 | −6619.3 |
| 42 | 8969.3 | 18117.8 | −9146.3 |
| 43 | 9360.4 | 27701.2 | −18338.6 |

TABLE 7D

Mouse Pair - D

| Day | Total Tumor Volume ($mm^3$) (Experimental) | Total Tumor Volume ($mm^3$) (Control) | Total Tumor Volume ($mm^3$) (Experimental minus Control) |
|---|---|---|---|
| 1 | 572.2 | 333.1 | 239.1 |
| 2 | 492.8 | 288.7 | 204.1 |
| 3 | 463.3 | 268.1 | 195.2 |
| 4 | 421.2 | 278.3 | 142.9 |
| 5 | 477.9 | 278.3 | 199.6 |
| 6 | 606.2 | 333.1 | 273.1 |
| 7 | 623.6 | 448.9 | 174.7 |
| 8 | 838.6 | 407.7 | 430.9 |
| 9 | 755.5 | 675.5 | 80.1 |
| 10 | 735.7 | 642.5 | 93.1 |
| 11 | 860.3 | 1018.9 | −158.6 |
| 12 | 998.4 | 849.7 | 148.7 |
| 13 | 998.4 | 905.3 | 93.0 |
| 14 | 1259.9 | 937.4 | 322.5 |
| 15 | 1288.3 | 1636.1 | −347.7 |
| 16 | 1697.5 | 1490.0 | 207.5 |
| 17 | 1802.8 | 1788.8 | 14.0 |
| 18 | 1912.4 | 1777.0 | 135.4 |
| 19 | 1949.9 | 2258.2 | −308.3 |
| 20 | 2065.3 | 2327.4 | −262.1 |
| 21 | 2185.2 | 2213.7 | −28.4 |
| 22 | 2395.2 | 2376.5 | 18.7 |
| 23 | 2352.2 | 2287.9 | 64.3 |
| 24 | 2482.8 | 2438.7 | 44.1 |
| 25 | 2572.6 | 2995.5 | −422.9 |
| 26 | 2782.9 | 2969.5 | −186.6 |
| 27 | 2953.9 | 3869.2 | −915.3 |
| 28 | 3203.0 | 3645.8 | −442.8 |
| 29 | 3302.6 | 4051.0 | −748.4 |
| 30 | 3913.1 | 4121.3 | −208.2 |
| 31 | 3836.2 | 3978.0 | −141.9 |
| 32 | 4364.0 | 4435.7 | −71.7 |
| 33 | 4844.1 | 4734.2 | 110.0 |
| 34 | 4853.1 | 5037.2 | −184.1 |
| 35 | 5012.3 | 5348.2 | −335.9 |
| 36 | 6110.7 | 5689.9 | 420.8 |
| 37 | 7031.4 | 6195.6 | 835.8 |
| 38 | 7335.0 | 6803.9 | 531.1 |

TABLE 7D-continued

Mouse Pair - D

| Day | Total Tumor Volume ($mm^3$) (Experimental) | Total Tumor Volume ($mm^3$) (Control) | Total Tumor Volume ($mm^3$) (Experimental minus Control) |
|---|---|---|---|
| 39 | 7648.1 | 7565.7 | 82.4 |
| 40 | 7898.2 | 8279.7 | −381.5 |
| 41 | 9362.1 | 9656.6 | −294.5 |
| 42 | 12818.9 | 8306.5 | 4512.3 |
| 43 | 14134.9 | 8726 | 5408.9 |

TABLE 7E

Mouse Pair - E

| Day | Total Tumor Volume ($mm^3$) (Experimental) | Total Tumor Volume ($mm^3$) (Control) | Total Tumor Volume ($mm^3$) (Experimental minus Control) |
|---|---|---|---|
| 1 | 310.4 | 44.6 | 265.8 |
| 2 | 124.8 | 57.9 | 66.9 |
| 3 | 195.4 | 54.4 | 141.1 |
| 4 | 179.6 | 54.4 | 125.2 |
| 5 | 220.9 | 69.5 | 151.4 |
| 6 | 278.3 | 92.0 | 186.3 |
| 7 | 239.1 | 172.0 | 67.0 |
| 8 | 268.1 | 137.3 | 130.8 |
| 9 | 905.2 | 118.9 | 786.4 |
| 10 | 770.5 | 130.9 | 639.6 |
| 11 | 1355.0 | 130.9 | 1224.1 |
| 12 | 1534.4 | 268.1 | 1266.3 |
| 13 | 1517.0 | 220.9 | 1296.0 |
| 14 | 1800.0 | 299.4 | 1500.6 |
| 15 | 2056.5 | 239.1 | 1817.5 |
| 16 | 2023.5 | 268.1 | 1755.4 |
| 17 | 2903.4 | 333.1 | 2570.3 |
| 18 | 2594.7 | 310.4 | 2284.4 |
| 19 | 2575.7 | 268.1 | 2307.6 |
| 20 | 2878.6 | 288.7 | 2589.9 |
| 21 | 2823.3 | 288.7 | 2534.6 |
| 22 | 3006.9 | 321.6 | 2685.4 |
| 23 | 3295.4 | 394.6 | 2900.8 |
| 24 | 3382.1 | 381.7 | 3000.4 |
| 25 | 4354.5 | 477.9 | 3876.6 |
| 26 | 4229.5 | 523.6 | 3705.9 |
| 27 | 4776.2 | 508.1 | 4268.1 |
| 28 | 5015.9 | 572.2 | 4443.7 |
| 29 | 5814.5 | 492.8 | 5321.7 |
| 30 | 6473.5 | 606.2 | 5867.3 |
| 31 | 6854.6 | 589.0 | 6265.6 |
| 32 | 7808.1 | 477.9 | 7330.2 |
| 33 | . | . | . |
| 34 | . | . | . |
| 35 | 9146.7 | 623.6 | 8523.1 |
| 36 | 11442.3 | 492.8 | 10949.5 |
| 37 | 12232.6 | 407.7 | 11824.9 |
| 38 | 11782.7 | 463.3 | 11319.4 |
| 39 | 13772.0 | 523.6 | 13248.4 |
| 40 | 12930.7 | 492.8 | 12437.9 |
| 41 | 12956.9 | 641.5 | 12315.4 |
| 42 | 11366.0 | 606.2 | 10759.9 |
| 43 | 12249.8 | 659.6 | 11590.2 |
| 44 | 12659.3 | 860.3 | 11799.0 |
| 45 | 16331.0 | 589.0 | 15742.0 |
| 46 | 15739.3 | 641.5 | 15097.9 |
| 47 | 16113.9 | 796.4 | 15317.5 |
| 48 | 20652.9 | 755.5 | 19897.4 |
| 49 | 22318.7 | 882.4 | 21436.3 |
| 50 | 22676.6 | 1204.3 | 21472.3 |
| 51 | 22641.9 | 838.6 | 21803.2 |
| 52 | 23486.9 | 904.8 | 22582.0 |
| 53 | 23103.4 | 1022.7 | 22080.7 |
| 54 | 24463.0 | 838.6 | 23624.4 |

TABLE 7F

Mouse Pair - F

| Day | Total Tumor Volume (mm³) (Experimental) | Total Tumor Volume (mm³) (Control) | Total Tumor Volume (mm³) (Experimental minus Control) |
|---|---|---|---|
| 1 | 623.6 | 38.8 | 584.9 |
| 2 | 492.8 | 87.1 | 405.7 |
| 3 | 735.7 | 258.2 | 477.5 |
| 4 | 696.9 | 220.9 | 476.0 |
| 5 | 775.8 | 1149.0 | −373.3 |
| 6 | 882.4 | 1064.5 | −182.1 |
| 7 | 817.3 | 1163.3 | −346.0 |
| 8 | 860.3 | 1059.8 | −199.5 |
| 9 | 882.4 | 1178.1 | −295.7 |
| 10 | 838.6 | 1184.6 | −346.0 |
| 11 | 1346.4 | 1266.3 | 80.2 |
| 12 | 1317.2 | 1289.2 | 28.0 |
| 13 | 1376.1 | 2092.2 | −716.1 |
| 14 | 1406.3 | 1947.9 | −541.7 |
| 15 | 1406.3 | 1856.8 | −450.5 |
| 16 | 1436.8 | 2000.7 | −563.9 |
| 17 | 2026.4 | 1926.2 | 100.2 |
| 18 | 1949.9 | 2077.2 | −127.3 |
| 19 | 2226.2 | 2302.4 | −76.2 |
| 20 | 2226.2 | 2286.7 | −60.5 |
| 21 | 2226.2 | 2549.1 | −322.8 |
| 22 | 2352.2 | 2556.7 | −204.5 |
| 23 | 2711.2 | 3476.0 | −764.8 |
| 24 | 2572.6 | 3196.8 | −624.2 |
| 25 | 2664.4 | 3781.6 | −1117.1 |
| 26 | 2806.3 | 3762.8 | −956.5 |
| 27 | 3764.4 | 4024.8 | −260.4 |
| 28 | 3315.4 | 4294.7 | −979.3 |
| 29 | 4064.6 | . | . |
| 30 | 4189.0 | . | . |
| 31 | 4577.4 | 4657.5 | −80.1 |
| 32 | 4849.3 | 4448.0 | 401.3 |
| 33 | . | 4753.6 | . |
| 34 | . | 4539.8 | . |
| 35 | 5424.9 | 6438.8 | −1013.9 |
| 36 | 5276.9 | 5834.5 | −557.6 |
| 37 | 5350.6 | 6359.7 | −1009.2 |
| 38 | 5651.9 | 5987.7 | −335.8 |

TABLE 7G

Mouse Pair - G

| Day | Total Tumor Volume (mm³) (Experimental) | Total Tumor Volume (mm³) (Control) | Total Tumor Volume (mm³) (Experimental minus Control) |
|---|---|---|---|
| 1 | 539.5 | 239.1 | 300.4 |
| 2 | 589.0 | 321.6 | 267.4 |
| 3 | 606.2 | 310.4 | 295.8 |
| 4 | 659.6 | 288.7 | 370.9 |
| 5 | 659.6 | 321.6 | 338.0 |
| 6 | 755.5 | 659.6 | 95.9 |
| 7 | 696.9 | 606.2 | 90.8 |
| 8 | 735.7 | 589.0 | 146.6 |
| 9 | 796.4 | 659.6 | 136.8 |
| 10 | 904.8 | 659.6 | 245.2 |
| 11 | 796.4 | 735.7 | 60.7 |
| 12 | 998.4 | 998.4 | 0.0 |
| 13 | 1098.1 | 904.8 | 193.3 |
| 14 | 1288.3 | 1531.2 | −242.9 |
| 15 | 1317.2 | 1499.3 | −182.1 |
| 16 | 1531.2 | 1406.3 | 124.9 |
| 17 | 1436.8 | 1596.3 | −159.5 |
| 18 | 1697.5 | 1912.4 | −214.9 |
| 19 | 1767.2 | 1838.9 | −71.6 |
| 20 | 1838.9 | 1949.9 | −111.0 |
| 21 | 1987.9 | 2309.7 | −321.8 |

TABLE 7H

Mouse Pair - H

| Day | Total Tumor Volume (mm³) (Experimental) | Total Tumor Volume (mm³) (Control) | Total Tumor Volume (mm³) (Experimental minus Control) |
|---|---|---|---|
| 1 | 623.6 | 1499.3 | −875.6 |
| 2 | 696.9 | 1596.3 | −899.4 |
| 3 | 696.9 | 2664.4 | −1967.5 |
| 4 | 755.5 | 1875.4 | −1119.9 |
| 5 | 1124.1 | 1912.4 | −788.4 |
| 6 | 1124.1 | 1629.6 | −505.5 |
| 7 | 927.6 | 2572.6 | −1644.9 |
| 8 | 998.4 | 2854.7 | −1856.3 |
| 9 | 1047.4 | 3315.4 | −2268.0 |
| 10 | 1563.5 | 5060.1 | −3496.6 |

The foregoing statistics of Example II may be summarized as follows:

EXAMPLE II STATISTICAL SUMMARY TABLE

| Mouse Pair | (E-C Tumor Vol.) Slope ($\hat{B}i$) mm³ Per Day | Standard Error of Slope (SE(($\hat{B}i$)) |
|---|---|---|
| XI-A | −.248 | 22.804 |
| XI-B | −46.27 | 14.331 |
| XI-C | −202.617 | 34.228 |
| XI-D | 24.345 | 13.302 |
| XI-E | 436.119* | 22.083 |
| XI-F | −22.894 | 6.234 |
| XI-G | −28.45 | 4.126 |
| XI-H | −205.533 | 76.213 |

—*p > .95 based on t-distribution of data (This entry was removed for the signficance test, the results of which are hereinafter summarized, because the entry is clearly aberrant).

The data in the above Example II Statistical Summary Table is subject to evaluation by a conventional significance test which indicates a strong anti-tumor efficacy for the XI pterin mixture. The mean difference (E-C Tumor Vol.) is $-68.80$ mm$^3$ per day. The values of this significance test are t (Student's t value)=$-5.41$; d f (degrees of freedom)=204; and p (probability level)<<0.000001.

SECOND EMBODIMENT

EXAMPLE III

In Example III, C3H/Ou mice, and thus of the same strain used in Example II, were handled in the test in the manner previously described relative to Example II. However, five mouse pairs were employed in Example III; that is, the mice were treated in pairs where one mouse of each pair was administered the pterin mixture and the other mouse of the pair was administered the same volume of Mammalian Ringer's Solution. However, in Example III, the test mice of the experimental group were administered a formulation of 32 micrograms per milliliter xanthopterin, 16 micrograms per milliliter isoxanthopterin and 16 micrograms per milliliter neopterin suspension in Mammalian Ringer's Solution hereinafter referred to for convenience as the "NX/pterin mixture".

The manner of data analysis was identical to that used with the XI pterin mixture of Example II. This experimental data is shown in the following tables.

TABLE 9A

Mouse Pair - A

| Day | Total Tumor Volume (mm$^3$) (Experimental) | Total Tumor Volume (mm$^3$) (Control) | Total Tumor Volume (mm$^3$) (Experimental minus Control) |
|---|---|---|---|
| 1 | 4989.2 | 606.2 | 4383.1 |
| 2 | 3862.3 | 589.0 | 3273.3 |
| 3 | 5123.5 | 477.9 | 4645.6 |
| 4 | 3862.3 | 606.2 | 3256.1 |
| 5 | 4845.9 | 659.6 | 4186.3 |
| 6 | 6930.8 | 696.9 | 6233.9 |
| 7 | 5722.8 | 796.4 | 4926.4 |
| 8 | 6341.9 | 796.4 | 5545.5 |
| 9 | 6616.4 | 796.4 | 5820.0 |
| 10 | 7338.5 | 817.3 | 6521.1 |
| 11 | 10179.2 | 838.6 | 9340.5 |
| 12 | 14424.5 | 860.3 | 13564.2 |
| 13 | 17098.8 | 882.4 | 16216.4 |
| 14 | 17497.5 | 1098.1 | 16399.3 |
| 15 | 21402.7 | 796.4 | 20606.3 |
| 16 | 21726.7 | 838.6 | 20888.1 |
| 17 | 22191.4 | 623.6 | 21567.7 |
| 18 | 28297.5 | 1150.4 | 27147.1 |
| 19 | 28643.6 | 1148.5 | 27495.1 |
| 20 | 30786.9 | 1172.9 | 29614.1 |
| 21 | 32817.0 | 1296.5 | 31520.6 |
| 22 | 37069.3 | 1360.6 | 35708.7 |
| 23 | 38558.2 | 1463.4 | 37094.9 |
| 24 | 37248.0 | 1644.1 | 35603.9 |
| 25 | 38051.4 | 1762.9 | 36288.5 |
| 26 | 39607.4 | 1908.3 | 27699.0 |
| 27 | 43239.5 | 1813.8 | 41425.7 |
| 28 | 39687.7 | 1850.5 | 37837.2 |

TABLE 9B

Mouse Pair - B

| Day | Total Tumor Volume (mm$^3$) (Experimental) | Total Tumor Volume (mm$^3$) (Control) | Total Tumor Volume (mm$^3$) (Experimental minus Control) |
|---|---|---|---|
| 1 | 1078.7 | 1070.2 | 8.5 |
| 2 | 1018.5 | 1380.9 | -362.4 |
| 3 | 994.4 | 1165.9 | -171.5 |
| 4 | 877.7 | 1176.7 | -299 |
| 5 | 1441.7 | 1652.6 | -210.9 |
| 6 | 1050.8 | 1869.7 | -818.9 |
| 7 | 1171.7 | 2030.9 | -859.2 |
| 8 | 1515.3 | 2103.8 | -588.5 |
| 9 | 1869.9 | 2226.2 | -356.3 |
| 10 | 1882.6 | 3069.8 | -1187.2 |
| 11 | 2331.3 | 3298.2 | -966.9 |
| 12 | 2415.1 | 3557.3 | -1142.2 |
| 13 | 2535.4 | 4266.8 | -1731.5 |
| 14 | 2756 | 5973 | -3217 |
| 15 | 2756.7 | 6924.7 | -4168 |
| 16 | 3092.7 | 8522.8 | -5430.1 |
| 17 | 3379 | 8759 | -5379.9 |
| 18 | 5278.3 | 8711.2 | -3433 |
| 19 | 6225.9 | 9009.9 | -2784.1 |
| 20 | 6340.5 | 8885 | -2544.5 |
| 21 | 7511.3 | 8425.5 | -914.2 |
| 22 | 8058.1 | 8751.9 | -693.8 |
| 23 | 8232.2 | 8720.6 | -488.4 |
| 24 | 8117.3 | 7751.8 | 365.5 |
| 25 | 8511 | 11362.3 | -2851.3 |
| 26 | 8486.9 | 9272.9 | -786 |
| 27 | 8212.9 | 10584.2 | -2371.3 |
| 28 | 8815.9 | 10332 | -1516.1 |
| 29 | 7906.1 | 13159 | -5253 |
| 30 | 8111.9 | 12437.5 | -4325.6 |
| 31 | 8956.5 | 15467.6 | -6511.1 |
| 32 | 8965.0 | 14752.3 | -5787.3 |
| 33 | 11431.6 | 14482.6 | -3051.0 |
| 34 | 11088.3 | 14989.3 | -3901.1 |
| 35 | 12205.5 | 15510.0 | -3304.5 |
| 36 | 11812.2 | 15462.8 | -3650.6 |
| 37 | 12983.4 | 19976.4 | -6993.0 |
| 38 | 13083.6 | 18174.3 | -5090.7 |
| 39 | 12175.5 | 19781.7 | -7606.1 |
| 40 | 12939.3 | 20298.9 | -7359.6 |
| 41 | 13124.9 | 23423.3 | -10298.4 |
| 42 | 13314.6 | 21624.1 | -8309.5 |
| 43 | 13993.6 | 22348.7 | -8355.1 |
| 44 | 13055.8 | 21663.4 | -8607.6 |
| 45 | 13828.6 | 24832.2 | -11003.6 |
| 46 | 13308.3 | 27425.4 | -14117.1 |
| 47 | 16061.2 | 27162.5 | -11101.3 |
| 48 | 15990.1 | 29932.2 | -13942.1 |
| 49 | 16520.8 | 28843.8 | -12323.0 |
| 50 | 17588.3 | 27662.1 | -10073.8 |
| 51 | 18759.5 | 28472.6 | -9713.1 |
| 52 | 16343.5 | 29533.8 | -13190.3 |
| 53 | 17201.8 | 30152.5 | -12950.7 |

TABLE 9C

Mouse Pair - C

| Day | Total Tumor Volume (mm$^3$) (Experimental) | Total Tumor Volume (mm$^3$) (Control) | Total Tumor Volume (mm$^3$) (Experimental minus Control) |
|---|---|---|---|
| 1 | 102.2 | 143.8 | -41.6 |

TABLE 9C-continued

Mouse Pair - C

| Day | Total Tumor Volume (mm³) (Experimental) | Total Tumor Volume (mm³) (Control) | Total Tumor Volume (mm³) (Experimental minus Control) |
|---|---|---|---|
| 2 | 97.0 | 229.9 | −132.9 |
| 3 | 118.9 | 137.3 | −18.4 |
| 4 | 143.8 | 150.5 | −6.7 |
| 5 | 164.6 | 137.3 | 27.4 |
| 6 | 150.5 | 179.6 | −29.1 |
| 7 | 278.3 | 124.8 | 153.5 |
| 8 | 220.9 | 164.6 | 56.3 |
| 9 | 477.9 | 220.9 | 257.0 |
| 10 | 448.9 | 195.4 | 253.5 |
| 11 | 606.2 | 203.7 | 402.5 |
| 12 | 589.0 | 212.2 | 376.8 |
| 13 | 1022.7 | 288.7 | 734.0 |
| 14 | 904.8 | 248.5 | 656.3 |
| 15 | 1150.4 | 258.2 | 892.2 |
| 16 | 1098.1 | 268.1 | 830.0 |
| 17 | 2618.2 | 239.1 | 2379.2 |
| 18 | 1802.8 | 268.1 | 1534.7 |
| 19 | 2664.4 | 333.1 | 2331.4 |
| 20 | 2352.2 | 381.7 | 1970.5 |
| 21 | 4380.3 | 394.6 | 3985.8 |
| 22 | 3591.5 | 407.7 | 3183.8 |
| 23 | 3591.5 | 463.3 | 3128.3 |
| 24 | 4644.4 | 589.0 | 4055.4 |
| 25 | 6370.9 | 735.7 | 5635.3 |
| 26 | 6623.5 | 966.4 | 5657.1 |
| 27 | 7238.6 | 1099.2 | 6139.4 |
| 28 | 9634.6 | 1302.0 | 8332.6 |
| 29 | 9203.2 | 1269.3 | 7934.0 |
| 30 | 9417.3 | 1317.4 | 8099.8 |
| 31 | 10079.2 | 1438.9 | 8640.3 |
| 32 | 11250.1 | 1489.2 | 9760.9 |
| 33 | 10653.9 | 1512.6 | 9141.3 |
| 34 | 9525.5 | 1752.1 | 7773.4 |
| 35 | 10421.5 | 1685.3 | 8736.1 |
| 36 | 10889.8 | 2582.6 | 8307.1 |
| 37 | 16997.8 | 2748.3 | 14249.4 |
| 38 | 12508.3 | 2885.3 | 9622.9 |
| 39 | 14422.5 | 3074.4 | 11348.1 |
| 40 | 18647.0 | 3171.7 | 15475.2 |
| 41 | 17975.1 | 3375.4 | 14599.7 |
| 42 | 24025.3 | 3426.5 | 20598.8 |

TABLE 9D

Mouse Pair - D

| Day | Total Tumor Volume (mm³) (Experimental) | Total Tumor Volume (mm³) (Control) | Total Tumor Volume (mm³) (Experimental minus Control) |
|---|---|---|---|
| 1 | 157.5 | 220.9 | −63.4 |
| 2 | 195.4 | 407.7 | −212.3 |
| 3 | 143.8 | 381.7 | −237.9 |
| 4 | 179.6 | 434.9 | −255.3 |
| 5 | 73.6 | 838.6 | −765.0 |
| 6 | 118.9 | . | . |
| 7 | 124.8 | . | . |
| 8 | 143.8 | 1047.4 | −903.6 |
| 9 | 118.9 | 838.6 | −719.8 |
| 10 | 143.8 | 950.8 | −807.0 |
| 11 | 150.5 | 796.4 | −645.8 |
| 12 | 187.4 | 998.4 | −810.9 |
| 13 | . | 882.4 | . |
| 14 | . | 589.0 | . |
| 15 | 299.4 | 523.6 | −224.2 |
| 16 | 321.6 | 678.1 | −356.5 |
| 17 | 407.7 | 775.8 | −368.0 |
| 18 | 321.6 | 882.4 | −560.8 |
| 19 | 333.1 | 927.6 | −594.6 |
| 20 | 434.9 | 1047.4 | −612.5 |
| 21 | 477.9 | 1022.7 | −544.8 |
| 22 | 477.9 | 1204.3 | −726.4 |
| 23 | 463.3 | 1098.1 | −634.9 |
| 24 | 572.2 | 1663.3 | −1091.1 |
| 25 | 838.6 | 1376.1 | −537.5 |
| 26 | 623.6 | 604.9 | 18.7 |
| 27 | 755.5 | 969.5 | −214.0 |
| 28 | 755.5 | 847.5 | −91.9 |
| 29 | 817.3 | 1261.8 | −444.4 |
| 30 | 882.4 | 1004.8 | −122.4 |
| 31 | 1072.6 | 994.6 | 78.0 |
| 32 | 950.8 | 1170.7 | −219.9 |
| 33 | 1022.7 | 1075.2 | −52.5 |
| 34 | 974.4 | 1004.4 | −30.0 |
| 35 | 1124.1 | 1340.9 | −216.9 |
| 36 | 1150.4 | 1643.8 | −493.4 |
| 37 | 1499.3 | 1950.3 | −451.0 |
| 38 | 1531.2 | 2082.0 | −550.8 |
| 39 | 1697.5 | 2072.7 | −375.2 |
| 40 | 1531.2 | 2369.8 | −838.6 |
| 41 | 1629.6 | 1808.2 | −178.6 |
| 42 | 1663.3 | 2101.2 | −437.9 |
| 43 | 1732.1 | 2197.9 | −465.7 |
| 44 | 1838.9 | 2655.2 | −816.4 |
| 45 | 1875.4 | 2636.1 | −760.7 |
| 46 | 2267.7 | 2985.8 | −718.1 |
| 47 | 1875.4 | 2840.5 | −965.1 |
| 48 | 1987.9 | 3005.7 | −1017.8 |
| 49 | 2185.2 | 2985.8 | −800.6 |
| 50 | 2226.2 | 3561.4 | −1335.2 |
| 51 | 2618.2 | 3741.6 | −1123.4 |
| 52 | 2664.4 | . | . |
| 53 | 2711.2 | . | . |
| 54 | 2854.7 | 3514.0 | −659.3 |
| 55 | 2758.5 | 3283.4 | −524.9 |
| 56 | 2711.2 | 3809.3 | −1098.1 |
| 57 | 2854.7 | 4153.6 | −1298.9 |
| 58 | 2806.3 | 4151.9 | −1345.6 |
| 59 | . | 5320.5 | . |
| 60 | . | 4880.5 | . |
| 61 | 3105.0 | 5865.7 | −2760.8 |
| 62 | 3003.2 | . | . |
| 63 | 3105.0 | . | . |
| 64 | 3105.0 | . | . |
| 65 | 3648.6 | 7261.4 | −3612.8 |
| 66 | 3823.2 | . | . |
| 67 | 3591.5 | . | . |
| 68 | 4003.3 | . | . |
| 69 | . | . | . |
| 70 | . | 9017.4 | . |
| 71 | . | . | . |
| 72 | 4189.0 | . | . |
| 73 | . | 9143.0 | . |
| 74 | . | . | . |
| 75 | . | 9680.9 | . |
| 76 | 6044.3 | . | . |
| 77 | . | . | . |
| 78 | . | . | . |
| 79 | . | 11959.7 | . |
| 80 | 6709.2 | . | . |
| 81 | . | . | . |
| 82 | 6370.9 | 12610.3 | −6239.3 |
| 83 | . | . | . |
| 84 | . | . | . |
| 85 | . | . | . |
| 86 | . | 18102.9 | . |
| 87 | . | . | . |
| 88 | . | . | . |
| 89 | 8580.7 | 16042.2 | −7461.6 |
| 90 | . | . | . |
| 91 | . | . | . |

TABLE 9D-continued

Mouse Pair - D

| Day | Total Tumor Volume (mm³) (Experimental) | Total Tumor Volume (mm³) (Control) | Total Tumor Volume (mm³) (Experimental minus Control) |
|---|---|---|---|
| 92 | . | . | . |
| 93 | 9744.5 | 15373.1 | −5628.6 |
| 94 | . | . | . |
| 95 | . | . | . |
| 96 | 11371.9 | 16453.0 | −5081.1 |
| 97 | . | . | . |
| 98 | . | 18568.1 | . |
| 99 | . | . | . |
| 100 | 9744.5 | 16093.6 | −6349.1 |
| 101 | . | . | . |
| 102 | . | . | . |
| 103 | 12121.5 | . | . |
| 104 | . | . | . |
| 105 | 12249.5 | 18032.9 | −5783.4 |

TABLE 9E

Mouse Pair - E

| Day | Total Tumor Volume (mm³) (Experimental) | Total Tumor Volume (mm³) (Control) | Total Tumor Volume (mm³) (Experimental minus Control) |
|---|---|---|---|
| 1 | 762.9 | 1911.2 | −1148.3 |
| 2 | 1142.2 | . | . |
| 3 | 1011.0 | . | . |
| 4 | 937.3 | 2696.6 | −1759.3 |
| 5 | 1252.2 | 2881.3 | −1629.1 |
| 6 | 1485.6 | 3376.8 | −1891.3 |
| 7 | 1398.6 | 3419.4 | −2020.8 |
| 8 | 1716.8 | 3911.6 | −2194.6 |
| 9 | 1509.2 | 4563.3 | −3054.1 |
| 10 | 1703.8 | 4497.2 | −2793.4 |
| 11 | 1626.7 | 5148.4 | −3521.8 |
| 12 | 1616.0 | . | . |
| 13 | 1628.7 | . | . |
| 14 | 1952.0 | . | . |
| 15 | 1981.1 | 8672.7 | −6691.7 |
| 16 | 2304.1 | . | . |
| 17 | 2363.3 | . | . |
| 18 | 2439.2 | . | . |
| 19 | 2324.2 | . | . |
| 20 | 3456.9 | 13903.9 | −10446.9 |
| 21 | 3459.5 | . | . |
| 22 | 3816.6 | . | . |
| 23 | 4284.1 | 16957.0 | −12672.9 |
| 24 | 4809.2 | . | . |
| 25 | 5088.2 | 17191.8 | −12103.6 |
| 26 | 4957.9 | . | . |
| 27 | 6899.4 | . | . |
| 28 | 6032.8 | . | . |
| 29 | 7741.9 | . | . |
| 30 | 8091.6 | . | . |
| 31 | 7091.0 | . | . |
| 32 | 8820.6 | 21209.1 | −12388.5 |
| 33 | 7972.0 | . | . |
| 34 | 10469.1 | . | . |
| 35 | 10690.2 | . | . |
| 36 | 11292.4 | 17926.6 | −6634.2 |
| 37 | . | . | . |
| 38 | . | . | . |
| 39 | 14226.2 | 22672.4 | −8446.2 |

The foregoing statistics of Example III may be summarized as follows:

EXAMPLE III STATISTICAL SUMMARY TABLE

| Mouse Pair | (E-C Tumor Vol.) Slope ($\hat{B}i$) mm³ Per Day | Standard Error of Slope ($SE((\hat{B}i))$) |
|---|---|---|
| NXI-A | 1605.185* | 70.956 |
| NXI-B | −240.865 | 18.998 |
| NXI-C | 391.485 | 26.075 |
| NXI-D | −56.799 | 5.363 |
| NXI-E | −284.623 | 58.212 |

—*p > .95 based on t-distribution of data (This entry was removed for the significance test, the results of which are hereinafter summarized, because the entry is clearly aberrant.)

The data in the above Example III Statistical Summary Table is subject to evaluation by a conventional significance test which indicates a strong anti-tumor efficacy for the NXI pterin mixture. The mean difference (E-C Tumor Vol.) is −47.70 mm³ per day. The values of this significance test are t (Student's t values)=−2.86; d f (degrees of freedom)=167; and p (probability level)<<0.005.

Analysis of the test data of the preceding Examples I, II and III reveals that the XI pterin mixture and the NXI pterin mixture seem to work better in some in vivo systems than in others. This may be because the active in vivo forms of these pterins are their di-hydro derivatives. It is well known that these reduced forms predominate in biological fluids. It is possible that the rodent strains which responded to the pterin formulations have more active pterin reductase systems that allowed the metabolic conversion of the pterins to their active in vivo forms.

Furthermore, it is anticipated that derivatives and analogs of xanthopterin, isoxanthopterin and neopterin will also exhibit similar anti-neoplastic activity. For example, 8-N-xanthopteriduim iodide, a synthetic derivative of xanthopterin, is currently being tested upon C3H/HeN-MTV +mice acquired from the National Institutes of Health of Frederick, Md. This derivative is being tested by adding the test compounds to the water ingested at liberty by the mice.

In this regard, the applicant believes to have synthesized an ethylated analog to xanthopterin and is presently ascertaining if the synthesized derivative is an enhanced anti-tumor agent using C3H/HeN-MTV+mice, using the following protocol.

Fifteen (15) female C3H/HeN-MTV+mice were purchased from the National Cancer Institute, Bethesda, Md. and induced with Dimethyl Benzanthracene (DMBA) at an early age to produce measurable tumors. After a period of acclimatization of about one (1) week, each mouse in the group began imbibing the test pterins; that is, 8-N Ethyl Xanthopteridium Iodide and a xanthopterin/isoxanthopterin mixture. This was done one (1) week prior to commencing carcinogen administration. The three groups of five mice received one of the following pterin mixtures in their drinking water: C—control (no pterins); XI—xanthopterin/ isoxanthopterin (2:1 Molar ratio); and N-ETHYL-xanthopteridium iodide (reaction mixture as described later). Each mouse received 1 mg DMBA in 0.1 mL cottonseed oil intragastrically every two weeks for a total of three doses. Each individual animal was palpated weekly, the presence and site of any breast tumors noted, the greater and lesser diameters of any tumor measured by caliper, and the information recorded on appropriate data sheets. Animals were sacrificed when any breast tumor exceeded 1 cm in diameter, or if the animal was in obvious physical distress. Results to date are very promising for the putative 8-N-ethyl xanthopteridium iodide being tested as hereinafter illustrated in Table 10.

TABLE 10

C3H/HeN-MTV + Mice

Kruskal-Wallis $X_1$: Group $Y_1$: Days Tumor Free

| | |
|---|---|
| DF | 2 |
| # Groups | 3 |
| # Cases | 12 |
| H | 3.626 |
| | p = .1632 |

Kruskal-Wallis $X_1$: Group $Y_1$: Days Tumor Free

| Group; | # Cases: | Σ Rank: | Mean Rank |
|---|---|---|---|
| Control | 3 | 19 | 6.333 |
| XI | 4 | 16 | 4 |
| N-Ethyl | 5 | 43 | 8.6 |

Mann-Whitney U $X_1$: Group $Y_1$: Days Tumor Free

| | Number: | Σ Rank: | Mean Rank: |
|---|---|---|---|
| XI | 4 | 12 | 3 |
| N-Ethyl | 5 | 33 | 6.6 |

| | |
|---|---|
| U | 2 |
| U-prime | 18 |

TABLE 10-continued

C3H/HeN-MTV + Mice

| | |
|---|---|
| Z | −1.96 |
| | p = .05 |

The p-value corresponding to the comparison between the XIpterin and 8-N-ethyl xanthopteridium iodide groups indicates that the derivatization of the xanthopterin significantly increased its anti-tumor efficacy relative to the XIpterin mixture.

Therefore, the anti-neoplastic compositions and methods for application thereof of the present invention are capable of therapeutically treating virtually all neoplasms regardless of the form, volume, location and state of development having application to Mammalian creatures with beneficial therapeutic results.

Although the invention has been herein shown and described in what is conceived to be the most practical and preferred embodiments, it is recognized that departures may be made therefrom within the scope of the invention which is not to be limited to the illustrative details disclosed.

Having described my invention, what I claim as new and desire to secure by Letters Patent is:

1. A method for treating mammary neoplasm or lymphocytic leukemia in a mammalian creature comprising administering to the creature a composition comprising a mixture of substantially about 32 micrograms per milliliter xanthopterin and substantially about 16 micrograms per milliliter isoxanthopterin suspension diluted in an inert carrier, applied in an amount of frequency sufficient to inhibit the growth of the neoplasm.

2. The method of claim 1 wherein said inert carrier is substantially about 0.2 milliliters Mammalian Ringer's Solution.

3. A composition useful for treatment of mammary neoplasm or lymphocytic leukemia consisting essentially of an effective amount of a mixture of substantially about 32 micrograms per milliliter xanthopterin and substantially about 16 micrograms per milliliter isoxanthopterin suspension diluted in an inert carrier.

4. The composition of claim 3 wherein said carrier is substantially about 3.0 milliliters Mammalian Ringer's Solution.

\* \* \* \* \*